US012589060B2

(12) United States Patent
Rabelo De Moraes et al.

(10) Patent No.: US 12,589,060 B2
(45) Date of Patent: Mar. 31, 2026

(54) BLEACHING POWDER COMPOSITION

(71) Applicant: KAO GERMANY GMBH, Darmstadt (DE)

(72) Inventors: Ines Rabelo De Moraes, Darmstadt (DE); Steven Breakspear, Darmstadt (DE); Peter Bauer, Darmstadt (DE); Bernd Nöcker, Darmstadt (DE)

(73) Assignee: KAO GERMANY GMBH, Darmstadt (DE)

( * ) Notice: Subject to any disclaimer, the term of this patent is extended or adjusted under 35 U.S.C. 154(b) by 667 days.

(21) Appl. No.: 17/771,671

(22) PCT Filed: Oct. 30, 2020

(86) PCT No.: PCT/EP2020/080484
§ 371 (c)(1),
(2) Date: Apr. 25, 2022

(87) PCT Pub. No.: WO2021/084055
PCT Pub. Date: May 6, 2021

(65) Prior Publication Data

US 2022/0370313 A1 Nov. 24, 2022

(30) Foreign Application Priority Data

Oct. 31, 2019 (EP) .................................... 19206394

(51) Int. Cl.

| | |
|---|---|
| ***A61K 8/22*** | (2006.01) |
| ***A61G 5/10*** | (2006.01) |
| ***A61K 8/02*** | (2006.01) |
| ***A61K 8/23*** | (2006.01) |
| ***A61K 8/25*** | (2006.01) |
| ***A61K 8/34*** | (2006.01) |
| ***A61K 8/41*** | (2006.01) |
| ***A61K 8/49*** | (2006.01) |
| ***A61Q 5/08*** | (2006.01) |
| ***A61Q 5/10*** | (2006.01) |

(52) U.S. Cl.
CPC .................. *A61K 8/22* (2013.01); *A61G 5/10* (2013.01); *A61K 8/022* (2013.01); *A61K 8/23* (2013.01); *A61K 8/25* (2013.01); *A61K 8/342* (2013.01); *A61K 8/415* (2013.01); *A61K 8/4953* (2013.01); *A61Q 5/08* (2013.01); *A61K 2800/31* (2013.01); *A61K 2800/43* (2013.01)

(58) Field of Classification Search
None
See application file for complete search history.

(56) References Cited

U.S. PATENT DOCUMENTS

| | | | | |
|---|---|---|---|---|
| 8,632,609 B2 * | 1/2014 | Wood | ....................... | A61K 8/42 8/111 |
| 2018/0235857 A1 | 8/2018 | Pressly et al. | | |

FOREIGN PATENT DOCUMENTS

| | | | | |
|---|---|---|---|---|
| DE | 10 2007 041493 A1 | 3/2009 | | |
| EP | 1970046 A1 * | 9/2008 | ........... | A61K 8/4953 |
| EP | 2 191 812 A1 | 6/2010 | | |
| EP | 2 559 456 A2 | 2/2013 | | |
| WO | WO-2009053180 A1 * | 4/2009 | ............... | A61K 8/22 |

OTHER PUBLICATIONS

Machine translation of the Description of EP 1970046A1.*
Machine translation of WO 2009/053180A1 (Year: 2025).*
International Search Report mailed Jan. 25, 2021, in connection with PCT International Application No. PCT/EP2020/080484.
Written Opinion issued in connection with PCT International Application No. PCT/EP2020/080484.

* cited by examiner

*Primary Examiner* — H. Sarah Park
(74) *Attorney, Agent, or Firm* — Norris McLaughlin, PA

(57) ABSTRACT

Bleaching powders, kits-of-parts for bleaching, and bleaching methods comprise at least xanthine and/or xanthine derivatives, wherein it was unexpectedly found that xanthine and/or xanthine derivatives in bleaching powder reduce damage to keratin fibers during bleaching methods or processes.

12 Claims, No Drawings

BLEACHING POWDER COMPOSITION

This application is the U.S. National Stage of International Application No. PCT/EP2020/080484, filed Oct. 30, 2020, which claims foreign priority benefits under 35 U.S.C. § 119 of European Application No. 19206394.9, filed Oct. 31, 2019, the disclosures of which are incorporated herein by reference.

FIELD OF THE INVENTION

The present invention is directed to a bleaching powder, kit-of-parts for bleaching, and bleaching method.

BACKGROUND OF THE INVENTION

Changing hair color (natural or artificially colored) can give a new fresh look, improve the self-image, and/or promote enhancement of self-esteem of clients. In most cases to get another hair color, the present hair color must be lifted, especially for changing from a brown or dark brown/black to a light shade. Therefore, bleaching is widely used for whole head coloring or lightening, as well for partial treatments such as highlights. Often a high lightening is desired. However, during the bleaching process reactive oxygen species (ROS) are formed which react with the hair fiber structure promoting both lifting in color, but also leading to undesirable hair damage.

EP2559456 and DE102007041493 disclose aqueous alkaline dyeing compositions comprising caffeine as adjuvant. However, the publications are silent on the core of the present invention.

WO2009053180 discloses aqueous oxidizing compositions comprising caffeine to reduce hair damage in perming processes. However, the publication is silent of the core of the present invention.

SUMMARY OF THE INVENTION

The first object of the present invention is a bleaching powder composition comprising:

a) one or more persalt(s) and/or peroxy salt(s), b) one or more alkalizing agent(s), c) one or more compound(s) according to the following structure:

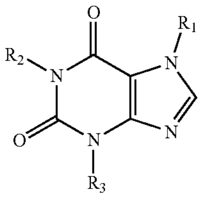

wherein $R_1$, $R_2$, and $R_3$ are independently selected from H and $CH_3$, and/or their mixtures.

The second object of the present invention is a two-part bleaching composition comprising:

a first bleaching powder composition A as defined above, and a second aqueous oxidizing composition B.

The third object of the present invention is a kit-of-parts comprising a first bleaching powder composition A as defined above, and a second aqueous oxidizing composition B, and optionally one or more compositions comprising oxidative dye precursors and/or oxidative dye couplers.

The third object of the present invention is the use of one or more compound(s) according to the following structure:

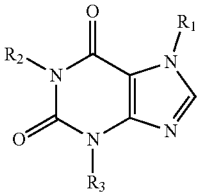

wherein $R_1$, $R_2$, and $R_3$ are independently selected from H and $CH_3$, and/or their mixtures, for reducing hair damage of bleaching compositions.

The fourth object of the present invention is a method for bleaching and/or lightening of keratin fibers, preferably human keratin fibers, more preferably human hair, comprising the steps of:

i) providing the composition as defined above and mixing it with an aqueous oxidizing composition having a pH in the range of 1 to 6 to yield a ready-to-use composition having a pH in the range of 7 to 12, ii) applying the ready-to-use composition onto keratin fibers and leaving it for a time period of 1 min to 60 min, iii) rinsing-off the keratin fibers with water and optionally shampooing the keratin fibers.

The fifth object of the present invention is a method for oxidative dyeing of keratin fibers, preferably human keratin fibers, more preferably human hair, comprising the steps of:

iv) providing the composition as defined above and mixing it with an aqueous oxidizing composition having a pH in the range of 1 to 6 to yield a ready-to-use composition having a pH in the range of 7 to 12, v) applying the ready-to-use composition onto keratin fibers and leaving it for a time period of 1 min to 60 min, vi) rinsing-off the keratin fibers with water and optionally shampooing the keratin fibers, vii) providing an oxidative dyeing composition comprising one or more oxidative dye coupler and/or one or more oxidative dye precursor and having a pH in the range of 7 to 12, viii) mixing the composition of step vii) with an aqueous oxidative composition to form a ready-to-use dyeing composition having a pH in the range of 7 to 12, ix) applying the ready-to-use dyeing composition onto keratin fibers and leaving it for a time period of 1 min to 60 min, x) repeating step vi).

DETAILED DESCRIPTION OF THE INVENTION

Inventors of the present invention have unexpectedly found out that the addition of xanthine derivatives to bleaching powder reduces damage to keratin fibers while maintaining a similar degree of lightening. Furthermore, the cosmetic appearance and properties of the keratin fibers are improved.

Bleaching Powder Composition

The present invention is directed to a bleaching powder composition comprising:

a) one or more persalt(s) and/or peroxy salt(s),
b) one or more alkalizing agent(s),
c) one or more compound(s) according to the following structure:

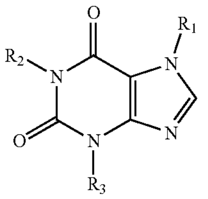

wherein $R_1$, $R_2$, and $R_3$ are independently selected from H and $CH_3$, and/or their mixtures.

The bleaching powder composition comprises one or more persalt(s) and/or peroxy salt(s). Suitable persalts and/or peroxy salts are sodium persulfate, potassium persulfate, ammonium persulfate, earth alkali peroxides such as magnesium peroxide, melamine peroxide or urea peroxide or phthalimidoperoxy hexanoic acid. The preferred persalts from the viewpoint of bleaching power are sodium, potassium, and ammonium persulfate.

It is preferred from the viewpoint of bleaching power and cosmetic safety that the total concentration of persalts and/or peroxy salts in the bleach powder composition is in the range of 10% to 80% by weight, preferably 15% to 70% by weight, more preferably 20% to 60% by weight, and still more preferably 25% to 60% by weight, calculated to the total weight of the bleach powder composition.

The composition further comprises one or more alkalizing agent(s) as compounds according to b). Preferably, the compounds according to b) are selected from inorganic and/or organic alkalizing agent(s), and/or their mixtures.

It is preferred from the viewpoint of powder stability and bleaching power that the compounds according to b) are inorganic alkalizing agent(s), preferably selected from metasilicates, carbonates, and/or bicarbonates, and/or their alkali or earth alkali salts, and/or their mixtures, more preferably the compound according to b) is sodium metasilicate.

It is preferred from the viewpoint of alkalinity that the compounds according to b) are organic alkalizing agent(s), preferably selected from alkyl- or alkanolamines according to the general structure

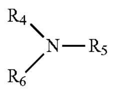

wherein $R_4$, $R_5$, and $R_6$ are same or different H, from $C_1$ to $C_4$, $C_3$ to $C_4$ unsaturated alkyl, $C_3$ to $C_4$ branched alkyl, $C_1$ to $C_4$ hydroxyl alkyl, $C_3$ to $C_4$ unsaturated hydroxyl alkyl, $C_3$ to $C_4$ branched hydroxyl alkyl, with the condition that at least one of $R_4$, $R_5$, or $R_6$ is different from H, and/or their mixtures.

Suitable organic alkalizing agents are monoethanolamine, diethanolamine, triethanolamine, monomethylamine, dimethylamine, trimethylamine, monoethylamine, diethylamine, trimethylamine, and 2-aminomethyl propanol.

The most preferred organic alkalizing agent(s) as compounds according to b) are selected from monoethanolamine and/or 2-aminomethyl propanol.

It is preferred from the viewpoint of alkalinity and powder stability that the composition comprises one or more compound according to b) at a total concentration in the range of 0.25% to 30% by weight, preferably 0.5% to 25% by weight, more preferably 1% to 20% by weight, calculated to the total weight of the composition.

Optionally, the bleach powder composition may comprise one or more ammonium salt(s) different from persalt(s) and peroxy salt(s).

Suitable ammonium salts different from persalt(s) and peroxy salt(s) are ammonium carbonate, ammonium hydrogen carbonate, ammonium carbamate, ammonium chloride, ammonium sulfate, ammonium phosphates, ammonium nitrate, ammonium bromide, ammonium iodide, ammonium thiosulfate, ammonium molybdate, ammonium vanadate, ammonium sulfamate, ammonium citrate, ammonium salicylate, ammonium valerate, ammonium tartarate, ammonium benzoate. ammonium acetate, ammonium formiate and ammonium lactate. Compositions may also comprise mixtures of ammonium salts.

The bleach powder composition may comprise one or more ammonium salts different from persalt(s) and peroxy salt(s) at a total concentration in the range of 0.1% to 10% by weight, calculated to the total weight of bleach powder composition.

The bleach powder composition comprises one or more compound(s) according to the following structure:

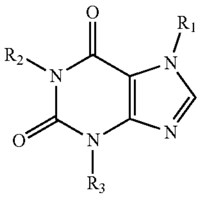

wherein $R_1$, $R_2$, and $R_3$ are independently selected from H and $CH_3$, and/or their mixtures, as compound(s) according to c).

Suitable compounds according to c) are xanthine and/or xanthine derivatives, preferably with the following substitution:

Xanthine with $R_1=R_2=R_3=H$,
Theobromine with $R_1=R_3=CH_3$ and $R_2=H$,
Theophylline with $R_2=R_3=CH_3$ and $R_1=H$, and
Caffeine with $R_1=R_2=R_3=CH_3$.
Mixtures of the above are suitable as well.

It is preferred from economic viewpoint and bleaching power that at least one compound according to c) is caffeine.

It is further preferred from the viewpoint of bleaching power that the total concentration of compounds according to c) is 0.001% by weight or more, more preferably 0.01% by weight or more, further more preferably 0.04% by weight or more, calculated to the total weight of the composition.

It is further preferred from the viewpoint of economic reasons as well as bleaching power that the total concentration of compounds according to c) is 2% by weight or less, more preferably 1.5% by weight or less, further more preferably 1% by weight or less, still more preferably 0.04% by weight or less, calculated to the total weight of the composition.

For attaining the above-mentioned effects it is preferred that the total concentration of compounds according to c) is in the range of 0.001% to 2% by weight, preferably 0.01% to 1.5% by weight, more preferably 0.04% to 1% by weight, still more preferably 0.04% to 0.2% by weight, calculated to the total weight of the composition.

Preferably, the bleach powder composition comprises less than 5% by weight of water, more preferably it is an anhydrous composition, from the viewpoint of stability and maintaining a free-flowing powder. The term anhydrous is to be understood that no water is added to the powder. However, this does not exclude any water bound to the ingredients by, for example, capillary forces.

It is further preferred from the viewpoint of cosmetic safety that the bleaching powder composition is dust-free. This property can commonly be achieved by adding lipophilic compounds to the bleach powder. From this viewpoint, the composition comprises one or more lipophilic compound(s) as compound according to d).

Preferably, the compound according to d) is selected from $C_{12}$ to $C_{22}$ fatty alcohols, esters of $C_3$ to $C_{12}$ alcohols with $C_{12}$ to $C_{22}$ fatty acids, $C_8$ to $C_{22}$ fatty acids, vegetable oils, and/or silicones, and/or hydrocarbon-based products, and/or their mixtures.

Suitable $C_{12}$ to $C_{22}$ fatty alcohols are myristyl alcohol, cetyl alcohol, stearyl alcohol, behenyl alcohol, and cetearyl alcohol.

Suitable esters of $C_3$ to $C_{22}$ alcohols with $C_{12}$ to $C_{22}$ fatty acids are isopropyl myristate, isopropyl palitate, and myristyl myristate.

Suitable $C_8$ to $C_{22}$ fatty acids are oleic acid, linoleic acid, and palmitic acid.

Suitable vegetable oils are olive oil, almond oil, sunflower oil, and argan oil.

Suitable silicones are non-aminated and/or aminated silicones. The latter are commonly known as amodimethicones.

Suitable hydrocarbon-based products are mineral oil, paraffins, and Vaseline.

It is preferred from the viewpoint of making the composition dust-free or formulating it as a paste that the concentration of compounds according to d) is in the range of 1% to 20% by weight, preferably 2% to 15% by weight, more preferably 3% to 12% by weight, calculated to the total weight of the composition.

Surfactants as Compounds According to e)

The bleaching powder composition of the present invention may further comprise one or more surfactant(s) as compound according to d), preferably selected from non-ionic surfactants, anionic surfactants, cationic surfactants, and/or amphoteric/zwitterionic surfactants, and/or their mixtures, more preferably selected from anionic surfactants and/or non-ionic surfactants, from the viewpoint of stabilizing the composition and improving wettability and mixability.

Preferably, the anionic surfactants may be selected from ethoxylated or non-ethoxylated alkyl ether sulfate surfactants, alkyl sulfates, ethoxylated and/or non-ethoxylated alkyl carboxylates, ethoxylated or non-ethoxylated amino acid surfactants, and/or their mixtures.

Suitable examples are alkyl sulfate or preferably ethoxylated alkyl ether sulfate surfactant or mixtures thereof having an alkyl chain length of $C_{10}$ to $C_{22}$.

Suitable non-ionic surfactants may be selected from alkyl polyglycosides, ethoxylated triglycerides, ethoxylated fatty alcohols, ethoxylated fatty acid esters, and/or their mixtures.

Suitable cationic surfactants are quaternary ammonium surfactants having a carbon chain length in the range of $C_{12}$ to $C_{22}$ or surfactants having a tertiary amine group and at least one alkyl chain having a carbon chain length in the range of $C_{12}$ to $C_{22}$ such as alkylamidoalkylamine surfactants. Suitable examples are cetrimonium chloride.

Suitable amphoteric/zwitterionic surfactants are of betaine type. Suitable compounds may be selected from alkyl betaines and/or alkylamido betaines. A preferred compound selected from alkyl betaines is lauryl betaine. A preferred compound selected from alkylamido betaines is cocamidopropyl betaine. The disclosure also relates to the salts of the compounds.

Suitable concentration ranges for surfactants are in the range of 0.1% to 10% by weight, calculated to the total weight of the composition

Thickening Polymers

In case the viscosity after mixing with other compositions needs to be further adjusted to prevent dripping, the bleach powder composition may comprise one or more thickening polymers, from the viewpoint of cosmetic safety.

The composition of the present invention comprises one or more thickening polymer(s) selected from non-ionic thickening polymers and/or anionic thickening polymers, and/or their mixtures.

Preferably, the thickening polymers are selected from polymers resulting in an aqueous solution and/or aqueous dispersion at pH between 1 and 6 having a viscosity of at least 1,000 mPa·s measured at a polymer concentration of 1% by weight in water at 25° C., calculated to the total weight of the composition, determined by a Brookfield viscometer, such as at 10 rpm for 1 min, with an appropriate spindle at 25° C.

Suitable non-ionic thickening polymers are cellulose-based polymers. Suitable examples of cellulose-based polymers are methylcellulose, hydroxymethylcellulose, hydroxyethylcellulose, hydroxypropylcellulose, hydroxyethyl-methylcellulose, and alkylated hydroxyl celluloses such as ($C_2$-$C_8$)-alkylcelluloses or cetyl hydroxyethylcellulose.

Suitable anionic thickening polymers are selected from naturally-based anionic polymers and/or synthetic anionic polymers.

Suitably, the natural anionic polymer(s) may be selected from xanthan gum, dehydroxanthan gum, hydroxypropylxanthan gum, carboxymethyl cellulose and starch based polymers such as vegetable starch and/or their synthetically modified derivatives such as hydroxypropyl starch phosphate. Equally suitable are alginic acids, sodium alginates, ammonium alginates, calcium alginates, gum arabic, and guar gum.

The preferred thickening polymer for the composition of the present invention are natural anionic polymers, more preferably xanthan gum and/or dehydroxanthan gum, from the viewpoint of their biodegradability and low environmental impact.

Preferably, the total concentration of thickening polymers of the present invention are 0.1% by weight or more, more preferably 0.25% by weight or more, more preferably 0.5% by weight or more, calculated to the total weight of the composition, from the viewpoint of providing sufficient viscosity to the composition.

Preferably, the total concentration of thickening polymers of the present invention are 15% by weight or less, more preferably 12% by weight or more, further more preferably 10% by weight or less, calculated to the total weight of the composition, from the viewpoint of providing sufficient viscosity to the composition and cost of goods.

For attaining the above-mentioned effects, it is preferred that the total concentration of thickening polymers in the composition of the present invention is in the range of 0.1% to 15% by weight, preferably 0.25% to 12% by weight, more preferably in the range of 0.5% to 10% by weight, calculated to the total weight of the composition.

Two-Part Composition

The present invention is also directed to a two-part composition comprising:

a first bleaching powder composition A as defined above, and a second aqueous oxidizing composition B.

The second aqueous oxidizing composition comprises one or more oxidizing agent(s). Preferably the oxidizing agent is hydrogen peroxide.

Suitable concentrations of the oxidizing agent(s), preferably hydrogen peroxide, in the aqueous oxidizing composition B is in the range of 1% to 20% by weight, more preferably 2% to 15% by weight, further more preferably 3% to 12% by weight, calculated to the total weight of the second part B composition.

Suitably, from the viewpoint of stability of the aqueous oxidizing composition B, the pH of the second part B composition is in the range of 1 to 6, more preferably 1.5 to 5, more preferably 2 to 4.5.

The pH may be adjusted with well-known acids such as phosphoric acid.

Kit-of-Parts

The present invention is also directed to a kit-of-parts comprising a first bleaching powder composition A as defined above, and a second aqueous oxidizing composition B, and optionally one or more compositions comprising oxidative dye precursors and/or oxidative dye couplers.

The second aqueous oxidizing composition may have the same features and characteristics as the second aqueous composition part B of the two-part composition.

The third composition comprising oxidative dye precursors and/or oxidative dye couplers is an oxidative dyeing composition and may further comprise one or more alkalizing agent(s). Preferably, this composition has a pH in the range of 7 to 12, more preferably in the range of 8 to 11, further more preferably 8.5 to 10.

Suitable alkalizing agents are ammonia and the alkalizing agents as present above for the bleaching powder composition. The concentration of alkalizing agents in the oxidative dyeing composition may be similar to the bleaching powder composition.

Use of Compound c)

The present invention is also directed to a use of one or more compound(s) according to the following structure:

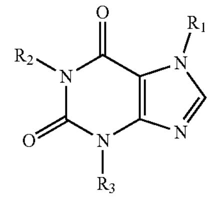

wherein $R_1$, $R_2$, and $R_3$ are independently selected from H and $CH_3$, and/or their mixtures, for reducing hair damage of bleaching compositions.

The preferred compound c) is caffeine. Thus, the invention is also directed to the use of caffeine for reducing hair damage of bleaching compositions.

The preferred concentration range is as disclosed for the bleaching powder composition.

Ready-to-Use Mixture and Method for Bleaching and/or Lightening

The present invention is also directed to a method for bleaching and/or lightening of keratin fibers, preferably human keratin fibers, more preferably human hair, comprising the steps of:

i) providing the composition as defined above and mixing it with an aqueous oxidizing composition having a pH in the range of 1 to 6 to yield a ready-to-use composition having a pH in the range of 7 to 12, ii) applying the ready-to-use composition onto keratin fibers and leaving it for a time period of 1 min to 60 min, iii) rinsing-off the keratin fibers with water and optionally shampooing the keratin fibers.

The bleach powder composition is mixed with the aqueous oxidizing composition to form a ready-to-use composition. Suitable mixing ratios by weight are 5:1 to 1:5 (bleach powder composition: aqueous oxidizing composition). Customarily, suitable mixing ratios are 1:1, 1:2, and 1:3 by weight (bleach powder composition: aqueous oxidizing composition).

Suitably, the pH of the ready-to-use composition is in the range of 7 to 12. It is preferred from the viewpoint of accelerated bleaching that the pH of the ready-to-use composition is in the range of 7.5 to 11, more preferably 8.0 to 10.5.

The ready-to-use composition is then applied to keratin fibers and left for a time period of 1 min to 60 min as defined in step ii). Preferred time ranges for step ii) are 5 min to 45 min, more preferred ranges are 10 min to 35 min, from the viewpoint of sufficiently bleaching the keratin fibers.

After that, the ready-to-use composition is rinsed-off from keratin fibers and optionally they are shampooed and optionally blow-dried.

Ready-to-Use Mixture and Method for Oxidative Dyeing

The present invention is also directed to a method for oxidative dyeing of keratin fibers, preferably human keratin fibers, more preferably human hair, comprising the steps of:

iv) providing the composition as defined above and mixing it with an aqueous oxidizing composition having a pH in the range of 1 to 6 to yield a ready-to-use composition having a pH in the range of 7 to 12, v) applying the ready-to-use composition onto keratin fibers and leaving it for a time period of 1 min to 60 min, vi) rinsing-off the keratin fibers with water and optionally shampooing the keratin fibers, vii) providing an oxidative dyeing composition comprising one or more oxidative dye coupler and/or one or more oxidative dye precursor and having a pH in the range of 7 to 12, viii) mixing the composition of step vii) with an aqueous oxidative composition to form a ready-to-use dyeing composition, ix) applying the ready-to-use dyeing composition onto keratin fibers and leaving it for a time period of 1 min to 60 min, x) repeating step vi).

Process steps iv) to vi) are identical to process steps i) to iii) and, therefore, the disclosure of the bleaching process is essentially the same for the bleaching process in combination with the oxidative dyeing process.

The oxidative dyeing composition of step vii) may be the same composition as disclosed for the kit-of-parts.

The following examples are to illustrate the invention, but not to limit it.

EXAMPLES

The following examples were prepared by subsequently adding each component to diatomaceous earth.

| Ingredient | Inventive example 1 | Inventive example 2 | Inventive example 3 | Inventive example 4 | Inventive example 5 | Comparative example 1 |
|---|---|---|---|---|---|---|
| | % by weight | | | | | |
| Potassium persulfate | 40.0 | 40.0 | 40.0 | 40.0 | 40.0 | 40.0 |
| Ammonium persulfate | 15.0 | 15.0 | 15.0 | 15.0 | 15.0 | 15.0 |
| Sodium metasilicate | 11.0 | 11.0 | 11.0 | 11.0 | 11.0 | 11.0 |
| Caffeine | 0.01 | 0.04 | 0.20 | 1.0 | 2.0 | — |
| Diatomaceous earth | Ad 100.0 | | | | | |
| ΔL | 50.0 | 47.9 | 48.8 | 50.0 | 49.4 | 49.4 |
| Damage [MPa] | 35.97 | 36.01 | 35.36 | 35.46 | 32.93 | 33.37 |
| ΔL/Damage [1/MPa] | 1.39 | 1.33 | 1.38 | 1.41 | 1.50 | 1.48 |

Methods

Bleaching Method

Caucasian hair streaks (21 cm, 2 g per bundle) were purchased from Fischbach+Miller Haar, Laupheim, Germany. The bleach powder compositions from above were mixed in a weight ratio of 1:2 (bleach powder: aqueous oxidizing composition) with an aqueous oxidizing composition comprising 9% by weight of hydrogen peroxide to prepare a ready-to-use composition. 1 g of the ready-to-use compositions were applied onto hair streaks and left for 30 min at 40° C. The hair streaks were then rinsed-off with lukewarm water, shampooed with a shampoo commercially available under the trade name Goldwell Deep Cleansing Shampoo, and blow-dried.

Lightening Measurements

L values were measured before and after bleaching with a Datacolor 45G instrument.

ΔL was calculated by subtracting the L value before bleaching from the L value after bleaching.

Damage Measurements

Damage was assessed, for twenty-five individual European hair fibres per treatment, via tensile test using an MTT680 instrument (Dia-Stron Limited, Andover, UK), in the wet condition. The initial sample length used was thirty millimetres and the strain rate was 100 percent per minute. The damage value is expressed as the stress (in MPa) at two percent strain, where the higher the number indicates less damage.

The following examples are within the scope of the present invention.

Example 6

Bleaching Powder Composition

| | % by weight |
|---|---|
| Hydroxyethylcellulose | 3 |
| Tetrasodium EDTA | 2 |
| Sodium carbonate | 1 |
| Ammonium persulfate | 11 |
| Potassium persulfate | 36 |
| Sodium metasilicate | 10 |
| Theobromine | 0.04 |
| Mineral oil | 8 |
| Diatomaceous Earth | to 100 |

The concentration of theobromine as compound according to c) may also be adjusted to 0.01%, 0.1%, 0.5%, 1.5% and 2% by weight or any values in between, above or below.

Example 7

Two Part Composition

Bleaching powder composition A

| | % by weight |
|---|---|
| Hydroxyethylcellulose | 3 |
| Tetrasodium EDTA | 2 |
| Sodium carbonate | 1 |
| Ammonium persulfate | 11 |
| Potassium persulfate | 36 |
| Sodium metasilicate | 10 |
| Caffeine | 0.04 |
| Mineral oil | 8 |
| Diatomaceous Earth | to 100 |

Aqueous oxidative composition B

| | % by weight |
|---|---|
| Cetearyl alcohol | 4.0 |
| Sodium lauryl sulfate | 0.8 |
| Phosphoric acid | q.s. ad pH 2.5 |
| Tetrasodium EDTA | 0.05 |
| Hydrogen peroxide | 6.0 |
| Water | ad 100.0 |

Example 8

Kit for Bleaching/Lightening and Oxidative Dyeing

The compositions A and B of example 7 are combined with the following oxidative dyeing composition:

| | % by weight |
|---|---|
| Cetearyl alcohol | 12 |
| Sodium cetearyl sulfate | 2 |
| Cocamide MEA | 5 |
| Oleic acid | 2 |
| Tetrasodium EDTA | 1 |
| Sodium sulfite | 1 |
| Ammonium hydroxide | 5 |
| Ammonium chloride | 1 |
| Toluene-2,5-Diamine sulfate | 0.75 |
| Resorcinol | 0.10 |
| 4-Chlorresorcinol | 0.25 |
| m-Aminophenol | 0.05 |
| 4-Amino-2-Hydroxytoluene | 0.05 |
| Fragrance | 0.5 |
| Water | ad 100 |

The above composition is adjusted to 9.5 by addition of NaOH/HCl.

The invention claimed is:

1. A bleaching powder composition comprising:

a) one or more persalts and/or one or more peroxy salts selected from the group consist of sodium persulfate, potassium persulfate, ammonium persulfate, earth alkali peroxides, phthalimidoperoxy hexanoic acid, and a mixture thereof;

b) one or more alkalizing agents selected from one or more metasilicates, one or more carbonates, one or more bicarbonates, their alkali or earth alkali salts, and a mixture thereof;

c) caffeine; and d) Diatomaceous earth, wherein a total concentration of the one or more persalts and/or one or more peroxy salts ranges from 10% to 80% by weight, calculated to a total weight of the bleaching powder composition, a total concentration of the one or more alkalizing agents ranges from 0.25% to 30% by weight, calculated to a total weight of the bleaching powder composition, a total concentration of the caffeine ranges from 0.001% to 1% by weight, calculated to the total weight of the bleaching composition, and the bleaching powder composition is an anhydrous composition comprising a free-flowing powder.

2. The bleaching powder composition of claim 1, wherein the bleaching powder composition comprises the one or more persalts and/or one or more peroxy salts at a total concentration ranging from 15% to 70% by weight, calculated to the total weight of the bleaching powder composition.

3. The bleaching powder composition of claim 1, wherein the bleaching powder composition comprises the one or more alkalizing agents at a total concentration ranging from of 0.5% to 25% by weight, calculated to the total weight of the bleaching powder composition.

4. The bleaching powder composition of claim 1, wherein the total concentration of the caffeine ranges from 0.01 to 1% by weight, calculated to the total weight of the beaching powder composition.

5. The bleaching powder composition according to claim 1, further comprising one or more ammonium salts different from the one or more persalts and the one or more peroxy salts.

6. The bleaching powder composition of claim 1, further comprising one or more lipophilic compounds.

7. The bleaching powder composition of claim 6, wherein the one or more lipophilic compounds are selected from $C_{12}$ to $C_{22}$ fatty alcohols, esters of $C_3$ to $C_{12}$ alcohols with $C_{12}$ to $C_{22}$ fatty acids, $C_8$ to $C_{22}$ fatty acids, vegetable oils, and/or silicones, and/or hydrocarbon-based products, and/or a mixture thereof.

8. The bleaching powder composition of claim 6, wherein the concentration of the one or more lipophilic compounds ranges from 1% to 20% by weight, calculated to the total weight of the bleaching powder composition.

9. A two-part bleaching composition comprising:

the bleaching powder composition of claim 1; and an aqueous oxidizing composition.

10. A kit-of-parts comprising the bleaching powder composition of claim 1;

an aqueous oxidizing composition; and one or more optional compositions comprising at least one of one or more oxidative dye precursors and one or more oxidative dye couplers.

11. A method comprising:

mixing the bleaching powder composition of claim 1 with an aqueous oxidizing composition having a pH ranging from 1 to 6 to produce or yield a ready-to-use composition having a pH ranging from 7 to 12;

applying the ready-to-use composition onto keratin fibers and leaving the ready-to-use composition on the keratin fibers for a time period of at least 1 minute and up to 60 minutes; and rinsing the ready-to-use composition off the keratin fibers with water, and optionally shampooing the rinsed keratin fibers.

12. The method of claim 11, further comprising:

providing an oxidative dyeing composition comprising at least one of one or more oxidative dye couplers and one or more oxidative dye precursors and having a pH ranging from 7 to 12;

mixing the oxidative dyeing composition with an aqueous oxidative composition to produce or form a ready-to-use dyeing composition having a pH ranging from 7 to 12;

applying the ready-to-use dyeing composition onto the keratin fibers and leaving the ready-to-use dyeing composition on the keratin fibers for a time period of at least 1 minute and up to 60 minutes; and optionally rinsing the ready-to-use dyeing composition off the keratin fibers.

* * * * *